United States Patent
De Luigi

(10) Patent No.: US 9,265,700 B2
(45) Date of Patent: Feb. 23, 2016

(54) METHOD FOR THE PREPARATION OF COLOURED COSMETIC POWDER PRODUCTS FOR USE ON THE SKIN OF THE EYES, FACE AND BODY

(71) Applicant: B.KOLORMAKEUP & SKINCARE S.R.L., Treviglio (IT)

(72) Inventor: Mario De Luigi, Milan (IT)

(73) Assignee: B.KOLORMAKEUP & SKINCARE S.R.L., Treviglio (BG) (IT)

( * ) Notice: Subject to any disclaimer, the term of this patent is extended or adjusted under 35 U.S.C. 154(b) by 108 days.

(21) Appl. No.: 13/787,467

(22) Filed: Mar. 6, 2013

(65) Prior Publication Data

US 2013/0236405 A1  Sep. 12, 2013

(30) Foreign Application Priority Data

Mar. 6, 2012  (IT) .............................. MI2012A0344

(51) Int. Cl.
*A61Q 1/10* (2006.01)
*A61Q 1/12* (2006.01)
*A61K 8/02* (2006.01)

(52) U.S. Cl.
CPC ............... *A61K 8/022* (2013.01); *A61K 8/0241* (2013.01); *A61Q 1/10* (2013.01); *A61Q 1/12* (2013.01); *A61K 2800/43* (2013.01)

(58) Field of Classification Search
None
See application file for complete search history.

(56) References Cited

U.S. PATENT DOCUMENTS

2003/0133895 A1 *  7/2003  China et al. ................ 424/70.12

FOREIGN PATENT DOCUMENTS

EP       2189150 A1    5/2010
JP       2001213727 A *  8/2001

OTHER PUBLICATIONS room temperature. Dictionary.com. Dictionary.com Unabridged. Random House, Inc.http://dictionary.reference.com/browse/room temperature (accessed: Mar. 23, 2015).*
Italian Search Report IT MI20120344 Dated December 3, 2012.
Extended European Search report dated Nov. 9, 2015.

* cited by examiner

*Primary Examiner* — Carlos Azupuru
*Assistant Examiner* — Casey Hagopian
(74) *Attorney, Agent, or Firm* — Hedman & Costigan, P.C.; James V. Costigan; Kathleen A. Costigan

(57) ABSTRACT

The present invention relates to a new method for the production of coloured cosmetic powders having a solid and creamy consistency for use on the skin of the eyes, face and body, to the powders of a solid and creamy consistency obtained with said production method and to their use as a cosmetic.

15 Claims, No Drawings

METHOD FOR THE PREPARATION OF COLOURED COSMETIC POWDER PRODUCTS FOR USE ON THE SKIN OF THE EYES, FACE AND BODY

The present invention relates to a new method for the production of coloured cosmetic powders having a solid and creamy consistency for use on the skin of the eyes, face and body.

Moreover, the present invention relates to the powders of a solid and creamy consistency obtained with the production method of the present invention. Such creamy solid powders, obtained in different colours, have the advantage of being able to be mixed to obtain new colours that were not present at the start of their production process, for example they can be assembled in different initial colours in the same container, i.e. the pan of the finished cosmetic product, and they are characterised in that they can be further mixed together to obtain new colours in the container in which they have been inserted. In this way, it is possible to obtain new creamy solid powders of a colour not present initially in the pan, equipped with excellent spreadability and hold after application on the skin.

Finally, the present invention relates to the cosmetic use of the solid coloured powders obtained with the process of the present invention for application on the skin of the eyes, the face or the body.

Solid powdered products currently available on the market come in various types, shapes, designs, colours, from simple one-colour to combinations of two or more colours, to complex multi-colour designs, in order to make which it is necessary to use techniques that combine, in a more or less precise and defined manner, the various parts that make up the design itself.

Such techniques make it possible to assemble many colours by mixing them together in a precise manner and according to a well-defined design or according to a random or non-homogeneous design. In any case, the colours that make up the products obtained with currently known technologies make it possible to obtain multi-colour products, where however the colours remain clearly distinct from one another, or where the number "n" of colours that makes up the product, whilst being assembled and/or mixed, remains separate and clearly visible and distinguishable from the one(s) next to it and remains the same number of colours present at the start of production or of use of the product.

Basically, the mixing of the coloured solid powders that make up the powders already known does not allow a new solid powder with a new colour to be obtained (chromatic staticity). The present invention allows this chromatic staticity to be overcome thanks to the choice of suitable components in certain proportions in the starting powder, like for example specific coloured pigments, hydrosoluble or liposoluble, ligands and surfactants, and of solvent subsequently added, as explained in detail hereafter.

Indeed, when an observer looks at one of the products currently on the market, he/she is always able to distinguish the "n" colours that make up the finished product, where by observer we mean any person not suffering from visual impairments that influence colour-perception, and not necessarily having cosmetic knowledge.

However creative and pleasing to the eye these products may be, they have the drawback of being "visually static", i.e. they are incapable of generating multi-tonal colour shades and/or being mixed to create new colours obtained by the mixing of two or more colours, where by new colours we mean colours that, although not having been prepared and inserted inside the product, are generated while it is made, by mixing of two or more colours: for example, green is produced by combining yellow and blue, even though green was not a colour foreseen or inserted originally in the finished product.

With the powders obtained according to the process of the present invention, on the other hand, cosmetic powders of solid consistency are obtained, by mixing which it is possible to create colour shades and new colour tones not initially present in the container (pan) that contains the powders obtained by the claimed process (thus obtaining a "chromatic dynamism").

The method for the production of coloured cosmetic powders having a solid and creamy consistency for use on the skin of the eyes, face and body object of the invention is a multi-phase process that comprises the addition of one or more solvents to a powder phase, containing at least one powder for cosmetic, alimentary and/or pharmaceutical use, one or more dyes, i.e. pigments for cosmetic use that may or may not be pearlescent, one or more ligands, which in turn contain at least one so-called "receiving liquid", which amongst other things can be an emulsifier. By "receiving liquid" we mean a liquid that has high affinity with the solvent that will be added after the compacting of the powder phase, and therefore the choice of the receiving liquid is carried out as a function of the solvent that will be added after said compacting. In particular the receiving liquid can be selected among emulsifiers, if the solvent added after compacting is selected from water, alcohols or hydroalcohol solutions, or it will be an apolar liquid, such as ethers, in particular propoxylated ethers, like for example PPG-15 stearylic ether or dicaprylic ether, if the solvent added after compacting is an organic solvent, like for example isododecane, isohexadecane, dodecane, hydrogenated didecene.

The receiving liquid, on the other hand, is selected among silicon/acrylate copolymers, like for example dimethicone acrylate or the copolymer acrylylate/tridecyl acrylate/triethoxysilylpropyl methacrylate/dimethicone methacrylate, when the solvent added after compacting is of the silicon type, i.e. a cyclomethicone or a disiloxane, such as cyclopentasiloxane, cyclohexasiloxane and/or methyl trimethicone, or a branched disiloxane.

The method for the production of coloured cosmetic powders having a solid and creamy consistency for use on the skin of the eyes, face and body object of the present invention comprises the following process phases:

a) mixing of the components of the powder phase, consisting of a percentage quantity of powders for cosmetic, alimentary and/or pharmaceutical use and of dyes ranging from 60% to 99.5% by weight, preferably equal to 80% by weight and a percentage quantity of ligand (or ligand mixture) and of receiving liquid (or mixture of receiving liquids) ranging from 0.5% to 40% by weight, preferably 20% by weight, where said percentages refer to the total weight of the powder phase; the percentage of receiving liquid present in the ligand ranges from 5% to 30% with respect to the total weight of the ligand, and preferably it is 10% by weight with respect to the total percentage quantity of ligand;

b) sieving, through a metallic net with a number of mesh openings (holes) of the sieve preferably within the range of 25 to 300 MESH and even more preferably 180 MESH;

c) assembly of the coloured powders thus obtained inside a container (pan);

d) compacting of the coloured powders inside the container through a pressure that varies within the range of 50 kPa to 20,000 kPa, preferably 10,000 kPa;
e) addition of a solvent to the compacted coloured powders obtained in point d), in a percentage quantity within the range of 10% to 50% by weight with respect to the total weight of the initial powder phase, and preferably it is 20% by weight, with respect to the total weight of the initial powder phase;
f) drying the product, with a drying temperature ranging from 25° to 100° C., preferably ranging from 25° to 40° C.

Optionally, after the assembly according to point c), the process of the present invention can comprise a further phase c') of mixing the coloured powders assembled inside the container.

Optionally, after the drying according to point f), the process of the present invention can comprise a further phase f') of removal of the surface of the compacted and dried powders in the container, to remove the surface layer.

By powders for cosmetic, alimentary and/or pharmaceutical use we mean the raw materials in powder form that can be selected from talcs, i.e. powders obtained from rocks finely ground until a granule size of between 2 and 40 microns is reached, chemically known as magnesium silicate hydrates, micas, or rather powders obtained from rocks finely ground until a granule size of between 2 and 40 microns is reached, chemically known as magnesium silicate hydrates and aluminium, acrylic polymers such as polymethyl methacrylate (PMMA), corn starch, sericite, silica, zinc stearate, cosmetic active principles, i.e. substances that have a very precise action on the skin, which is not purely decorative, like for example a bleaching action, thanks to the presence for example of azelaic acid or of kojoko acid, a detoxifying action, thanks to the presence for example of a green coffee extract, of an antioxidant action, thanks to the presence for example of tocopherol, of a hydrating action, thanks to the presence for example of hyaluronic acid, of a soothing action, thanks to the presence for example of allantoin, of a rubefacient action, thanks to the presence for example of benzyl nicotinate, preservatives, like for example sorbic acid and its salts, dehydroacetic acid and its salts, parahydroxybenzoates, phenoxyethanol, isothiazolinones, chlorophenesin, urea, formaldehyde cessors, for example imidazolidinyl-urea or diazolidinyl-urea, and/or substances having an antimicrobial and antifungal functionality, like for example para-anisin acid, cinnamic acid, short-carbon-chain derivatives of glycerol, for example glyceryl caprylate.

Some of these components of the powder phase, as is known in the field, can be able to modify the sensorial characteristics, such as softness to the touch, smoothness, slipperyness, or the application characteristics, such as ease of application, speed of application of the product, permanence on the skin, the matrix of the product itself, which is defined as "texture". These properties are held for example by PMMA, polymethylmethacrylate, silica, amides. Therefore, by the term "texturising" or "texture agent", in the jargon we indicate powders, from synthesis or of natural origin, capable of modifying the sensorial and/or application characteristics of the end product.

The ligands used in the present invention are raw materials for cosmetic, alimentary and/or pharmaceutical use in the form of liquids, pastes and/or waxes, both of natural or synthetic origin, with polar or apolar and/or preserving character and they are for example esters like esters of fatty acids and triglycerides, natural or synthetic waxes, alcohols, such as fatty alcohols, oil refining derivatives, silicon derivatives and mixtures thereof. In particular, the following ligands and/or mixtures thereof are preferred: phenyl dimethicone, dimethicone, carnauba wax, octyldodecanol, vaseline oil, isononyl isonanoate, isopropyl stearate, capric/caprilic triglyceride, phenoxyethanol and/or caprilyl dimethicone and mixtures thereof.

As already indicated above, the ligand must contain at least one "receiving liquid" or a mixture of "receiving liquids, where the receiving liquid is selected as a function of the solvent that will be added after compacting of the powder phase. The function of the receiving liquid is to promote the formation of a subsequent pseudo-emulsion where by the term "pseudo-emulsion" we mean an interaction between "receiving liquid(s)" and the solvent added after compacting itself, i.e. the interaction between the emulsifiers and the water or the alcohol and/or hydrophilic solutions added after compacting, or the interaction between the ethers and the organic solvents added after compacting or the interaction between the silicon/acrylate copolymers and the silicon solvent added after compacting. What is observed is not the formation of an actual emulsion, but an interaction that improves and promotes the diffusibility of the solvent, increasing the ability to "dissolve" the hydrophilic or lipophilic pigments of the dye or mixture of dyes initially added in the powder phase.

Indeed, the dyes present in the initial powder phase can be soluble or insoluble in the solvent added after compacting, and the receiving liquid present in the initial ligand will make it possible to adjust the solubility of the dyes in the solvent subsequently added and to adjust their possibility of further mixing to obtain new colours not initially present.

For example, the presence in the initial powder of one or more hydrosoluble dyes and of liposoluble dyes, and the use of water as solvent medium after compacting, will allow just the hydrosoluble pigments to be solubilized, keeping the lipophilic ones unaltered.

In this way, new coloured phases will be obtained that can be mixed to create new "multi-tonal" colouring effects.

The receiving liquid can have polar characteristics, i.e. it can be an emulsifier or surfactant with polar nature, like for example an emulsifier for W/O (water/oil) or O/W (oil/water) emulsions, like for example polysorbate-20, PEG-100 stearate, where by PEG we mean polyethylene glycol ester, sorbitan stearate, oleth-10 phosphate, and/or even polyglyceryl-2 isostearate, should water, alcohols or hydrophilic solvents be used as solvent for adding after compacting; or the receiving liquid can have an apolar nature, like for example carbon-based esters or ethers, for example propoxylated ethers like for example PPG-15 sterarylic ether when organic solvents are used as post-compacting solvent, or the receiving liquid can be a silicon/acrylate copolymer, like dimethicone acrylate, should it be wished to use a hydrocarbon organic solvent after compacting, like for example isododecane, or a silicon solvent, like a disiloxane, cyclopentasiloxane, cyclohexasiloxane, methyl trimethicone. Furthermore, the receiving liquids can be surfactants with amphiphile nature, like for example acrylates/C10-30 alkyl acrylates crosspolymer, acrylates/vinyl isodecanoate crosspolymer or inulin lauryl carbamate, should it be opted to have a mixture of water and glycols, like for example hexylene glycol, butylene glycol, propylene glycol or pentylene glycol, or hydrodispersible esters, like for example bis-ethoxyglycol succinate as post-compacting solvents.

According to the present invention, by dyes we mean powders containing coloured pigments, which can be non-pearlescent opaque coloured pigments, in the jargon "matte", i.e. synthesis dyes that from the chemical point of view comprise for example azoic derivatives (CI15985), xanthene derivatives (CI45170), anthraquinone derivatives (CI60725), triphenylmethane derivatives (CI42090), indigo derivatives (CI73015) and many others; in turn, such dyes divide into many classes, including: inorganic, iron oxides, titanium dioxide, chromium oxides and hydroxides, aluminium and sodium sulfur silicates, manganese violet, ferric ferrocyanide; "lacquers", i.e. dyes obtained by precipitation of a soluble dye on a substrate of aluminium and/or calcium and/or barium hydroxide; hydrosoluble dyes, i.e. water- or alcohol-soluble dyes, for example FD&C RED 33 (CI17200), FD&C RED 40 (CI16035), FD&C BLUE N° 1 (CI42090), where the abbreviation CI indicates the reference to the Colour Index International for a unique identification, or liposoluble dyes, i.e. soluble in oils and silicons for example, FD&C YELLOW N° 5 AL LAKE (CI19140) or iron oxides (CI77499, CI77491, CI77499); and finally they can also be natural dyes, i.e. not produced by chemical synthesis, but obtained from plants and/or rocks, by maceration, grinding, which include for example licopene, betacarotene, guanine, carmic acid, anthocyanins. Otherwise they can be pearlescent colouring pigments, i.e. natural dyes, organic and/or inorganic, deposited on a substrate of natural mica (muscovite), synthetic mica (fluorplogopite), borosilicate, where all of the quoted dyes are for cosmetic, alimentary and/or pharmaceutical use.

The dyes in general have a granule size that varies within the range of 3 to 40 microns with a mean of the gaussian distribution curve around 15-20 microns. However, it is also possible to use pearlescent pigments with a granule size ranging from 50 to 200 microns, in particular from 100 to 150 microns.

Such colouring pigments, which can be lipophilic or hydrophilic, of natural or synthetic origin, are, for example, the ones given hereafter, where the abbreviation CI indicates the reference to the Colour Index International for a unique identification: carmine (CI75470), titanium dioxide (CI77891), iron oxide (CI77491-CI77492-CI77499), fd&c blue n 1 (CI42090), red 33 hydro (CI17200), mica (CI77019)+TiO2 (CI77891), mica (CI77019)+iron oxide (CI77491-2-9), bismuth oxychloride (CI77163), mica (CI77019); d&c red 7 ca lake (CI15850:1), d&c red 30 al lake (CI73360), d&c yellow 5 al lake (CI19140:1); ultramarine blue (CI77007), and/or chromium hydroxide (CI77289).

As already indicated above, the initial powder phase consists of a percentage quantity of powders for cosmetic, alimentary and/or pharmaceutical use and of dyes ranging from 60% to 99.5% by weight, preferably equal to 80% by weight and a percentage quantity of ligand (or mixture of ligands) and of receiving liquid (or mixture of receiving liquids) ranging from 0.5% to 40% by weight, preferably 20% by weight, where said percentages refer to the total weight of the powder phase. The percentage of receiving liquid present in the ligand ranges from 5% to 30% with respect to the total weight of the ligand, and preferably it is 10% by weight with respect to the total percentage quantity of the ligand.

Preferably, the percentage of dyes initially present ranges from 0.05% to 60%, where these percentages refer to the percentage quantity of powders for cosmetic, alimentary and/or pharmaceutical use and of dyes of the initial powder phase; where preferably the percentage of soluble pigments ranges from 1% to 20% with respect to the total weight of the soluble and insoluble pigments. Preferably, the soluble pigments will be introduced at a percentage of 5% with respect to the total of the pigments present.

Phase a) of the process of the invention of mixing the powder phase can be carried out for example with a blade and/or knife mixer, used at variable speed. The speed of the blades or knives can vary within the range of 200 to 6000 revs/minute, according to the components of the powder phase, and the preferred number of revs/minute is 1500 revs/minute. It is necessary to obtain a homogeneous product in accordance with the process parameters, such as homogeneity of the compound, absence of lumps and/or spots of ligand not sufficiently dispersed, colouring matching the laboratory sample, microbiological analysis in line with the directives COLIPA, CTFA and CTPA, which regulate the cosmetics field, which indicate, depending on the type of product, its use and the end user, adult or child, the maximum limits of acceptability for a microorganism that is not pathogenic and the absence of specific microorganisms, including *P. aeruginosa, C. albicans, E. Coli*, absence of odours not in accordance with the laboratory sample, necessary for the subsequent processing phases.

The mixing operation can be carried out in a single cycle, or in many successive cycles. The number of cycles varies based on different factors, i.e.: type of product to be made, where by type of product to be made we mean a "matte" product, i.e. without pearlescent pigments, or "pearled" thus with pearlescent pigments: in the first case many processing cycles are necessary to allow the aforementioned requirements to be obtained, i.e. the processing cycles can range from 3 to 6 consecutive cycles lasting 15-30 minutes each; in the second case, i.e. for pearled products, in order to keep the gloss of the end product integral, the cycles could reduce to a range of between 1 and 4 cycles, lasting 5-15 minutes. Pearlescent pigments require a smaller number of processing cycles since the mechanical impact of the machine can damage the pearlescent pigments, drastically reducing its characteristic gloss effect. Another element that can influence the number of processing cycles is the amount of product, and therefore the mixing plant to be used. In general, the size (capacity expressed in litres or in kg) of the mixing plant will vary in relation to the amount of raw materials to be worked, and therefore the less the amount of raw material and the shorter the time and the smaller the number of mixings necessary.

The mixing times vary within the range of 1 to 90 minutes, for each cycle, preferably the time necessary for a correct mixing of the product ranges from 5 to 30 minutes and even more preferably it is 15 minutes divided over 2 mixing cycles, each lasting 7 minutes and 30 seconds.

Phase b) of the process of the invention of sieving through a metallic net can be carried out using a vibration and/or drum shaker, where the product is pushed by vibrating and/or rotating brushes through a metallic net allowing a purification of the product by removal of impurities or of the possible non-homogeneous parts. Preferably, the number of metallic mesh openings (holes) of the sieve is within the range of 25 to 300 MESH and even more preferably of 180 MESH, where by MESH we mean the unit of measurement that indicates the number of mesh openings (holes) per square inch.

Phase c) of the process of the invention provides for the automatic or manual assembly of the coloured powders obtained from phases a) and b) inside a container (pan), which can be metallic, made from plastic material and/or from terracotta.

Once placed in the container, the coloured powders obtained from phases a) and b) can be optionally further mixed together, as indicated in phase c'). Such mixing makes it possible to obtain a coloured effect in the jargon called "melange", where however the original colours of the powders are still clearly distinguishable from one another even if they have been mixed, since the colours have only been brought up to one another, but it is not possible to obtain the creation of new colours not initially present, since the addition of the solvent that creates the pseudo-emulsion has not yet taken place.

The optional mixing of phase c') can be carried out with manual mixers and/or automatic brushes that, by penetrating into the product through a predetermined movement, allow the colours to be mixed together. The predetermined movement can vary according to the number of colours foreseen by the end product and it will take place about a central axis. Such a movement can be of the linear, rotary or elliptical type, where a linear movement from right to left and vice-versa is preferred.

Phase d) of the process of the invention of compacting the coloured powders inside the container (pan) will be carried out through the application of a pressure that varies within the range of 50 kPa to 20,000 kPa, preferably 10,000 kPa. Such a pressure will be applied in one or more cycles to the powders, preferably 1 to 5 pressure application cycles, preferably 2 cycles, for a period of time for each application of pressure within the range of 1 to 100 tenths of a second, preferably 50 tenths of a second.

The pressure will for example be applied to the coloured powders to be compacted through an oil-hydraulic or electrodynamic compacting press.

Phase e) of the process of the invention foresees the addition of a solvent to the compacted coloured powders obtained in point d), in a percentage quantity within the range of 10% to 50% by weight with respect to the initial weight of the powder phase, and preferably it is 20% by weight, with respect to the initial weight of the "powder phase".

The amount of solvent used depends on the type and on the granule size of the dye that it is wished to solubilise in the pseudo-emulsion that is obtained after the addition of the solvent itself to the compacted powder phase.

For example, the presence in the initial powder phase of soluble dyes on an aluminium substrate (lacquers), or of chromium oxides, or of pearlescent pigments with granule size ranging from 5 to 25 microns, requires a greater amount of solvent, with respect to the presence of dyes such as iron oxides or titanium dioxides with pearlescent pigments with greater granule size, i.e. ranging from 100 to 150 microns.

The solvents used in the process of the present invention are selected in relation to the powders for cosmetic, alimentary and/or pharmaceutical use used and to the type of hydrosoluble or liposoluble dyes, the ligand and the emulsifier used and they are selected from petroleum derivatives, like for example hydrocarbon solvents, i.e. isoparaffins, cyclic paraffins, from silicons like volatile silicons, for example low-viscosity linear dimethicone dimers or trimers, such as disiloxanes and/or phenyltrimethicone, and from polar solvents, such as water, alcohols, such as isopropyl, ethyl, methyl alcohols and mixtures thereof.

The amount of solvent used varies within a range of 10% to 50% by weight, with respect to the initial weight of the powder phase, and preferably it is 20% by weight, with respect to the initial weight of the powder phase.

The receiving liquid present in the ligand in the powder phase has the function of allowing a better distribution of the ligand in the product and when the solvent is added to the compacted powder phase, the hydrosoluble or liposoluble dyes solubilize in the hydrophilic or lipophilic solvent added, according to their hydrophily/lipophily, thus creating new colours not initially present.

The addition of the solvent can for example be carried out through aerosol and/or spray, with immersion of the compacted pan in a bath of solvent or by direct addition of the solvent on the product through the use of a volumetric doser, where the immersion of the compacted pan in a bath of solvent is preferred.

Phase f) of the process of the invention, i.e. the drying of the product, is carried out with a drying temperature ranging from 25° to 100° C., preferably ranging from 25° to 40° C. This phase foresees the removal of the solvent added in the previous phase, so as to obtain a percentage of residual solvent ranging from 0.1% to 10%, preferably equal to 5% by weight with respect to the initial weight of the solvent added in phase "e". The percentages of residual solvent are evaluated through the use of a thermoscale.

The permanence times of the product in the drying phase vary as a function of the type of product to be made and they will be within the time ranges of 3 hours to 120 hours, preferably it will be a range of between 30 and 60 hours and even more preferably it will be a time of 48 hours.

The drying must not be carried out at a temperature of over 100° C.: indeed, it is necessary to avoid the complete drying of the product to allow the solvent to perform its solubilizing function on the dyes present in the pseudo-emulsion obtained after the addition of the solvent itself.

The drying can be carried out with conventional techniques, like for example the use of a stationary or dynamic drying oven.

Finally, the process of the invention can foresee a further optional phase f') for the removal of the surface of the compacted and dried powders in the pan, to remove the surface layer. Indeed, the drying of the solvent can sometimes create excessively hardened surface parts ("scales") that can hinder the subsequent taking of the end product from the pan. Said scales can form due to the evaporation of the solvent, which takes place from inside the product towards the outside. The possible formation of such a surface scaling, could make the product itself unusable, which would no longer be able to perform the decorative function. Indeed, the decorative make-up product must, as well as being pleasant to look at, also have optimal application qualities, in particular it must be simple to use, and last as long as possible on the skin, be it on the face or the body, as well as being homogeneous. In order for these qualities to be present it is necessary for the surface of the make-up product to be suitable for this purpose, i.e. it has to be free from scales that can make the product difficult to take or completely untakeable.

This optional removal of the product obtained after drying can be carried out with the help of special cutting tools, manual or automatic, and it can comprise a further compacting phase of the product in the pan, which can be carried out in the same way described for the compacting phase d).

Once the production process according to phases a)-f) described above and the possible phases c') and f') are completed, a microbiological check is carried out and then it proceeds to packaging and/or storage.

Therefore, the objects of the present invention are the production process according to phases a)-f) described above and the possible phases c') and f') described above, the coloured powders obtained through said process and the use of the solid coloured powders obtained with the process of the present invention as a cosmetic, for application on the skin of the eyes, face or body.

EXAMPLES

Formulation Examples and General Production Methods
N. 1: Compact Eye Shadow
Formulation

| DESCRIPTION OF RAW MATERIALS | QUANTITY (%) |
|---|---|
| PHASE A | |
| Talc (filler) | q.s. 100 |
| Mica (CI77019) (texturiser) | 15 |
| Corn starch (texturiser) | 10 |
| Ultramarine blue (CI77007) (insoluble dye) | 5 |
| FD&C Blue n°1 (CI42090) (soluble dye) | 3 |
| Carminex lake 52% (CI75470) (insoluble dye) | 10 |
| Titanium dioxide (CI77891) (insoluble dye) | 2 |
| Ethylene/acrylic acid copolymer (texturiser) | 1.5 |
| Polymethyl methacrylate (texturiser) | 7.5 |
| Silica (texturiser) | 1 |
| Sorbic acid (preservative) | 0.3 |
| Phase B | |
| Octyldodecanol (ligand) | 6.5 |
| Peg-12 dimethicone (receiving liquid) | 1.5 |
| Phenoxyethanol (ligand) | 0.85 |

Production of the Product of Example 1

Mixing of Phases A and B

After having carried out an accurate cleaning and sanitization operation of every part of the blade and/or knife mixer and all of the necessary tools, carried out manually by an operator with the help of sponges and/or disposable cleaning cloths soaked with ethylene alcohol and/or sanitizer, each raw material of phase A is weighed in a suitable container, like for example a plastic bag (PE). Every raw material before phase B is on the other hand weighed in a metal beaker, and then the content of the beaker is agitated (mechanically or manually) to obtain a uniform, limpid and homogeneous liquid.

Phases A and B obtained as outlined above are poured into the mixer and are mixed by setting two mixing cycles of 7 minutes and 30 seconds each. In order to better homogenise the end product, between one cycle and the next the mixer is opened and with a metallic or plastic spatula the residual powder and/or ligand left stuck to the walls, lid and bottom of the machine is removed.

Routine Checks After Mixing

After mixing, an amount of at least 100 g of product is taken for the necessary routine checks, such as checking that the colour matches the laboratory sample; absence of lumps in the compound; absence of spots of not correctly dispersed ligand (phase B), homogeneity of the surface of the product, absence of odours not present in the laboratory samples. If all of the checks satisfy the acceptability requirements the product is discharged into plastic bags; if one of such requirements is not met, the necessary corrections are made; for example if there are spots of undispersed ligand, then a further mixing is carried out lasting 7 minutes and 30 seconds; in the case for example of absence of spots of ligand but a colour that is too light with respect to the laboratory sample, further dyes are added and dispersed by mixing the powder for at least 5 minutes. Such an operation could be repeated "n" times until the sample colour is obtained.

Once the acceptability requirements of the product have been obtained, it is then discharged into PE bags ready for the subsequent processing phases. A sample of product is sent to the microbiological check for the analyses that ascertain the absence of pollutants, such as fungi, moulds, bacteria, yeasts, etc.

Compacting of the Mixed Powder

Once the described checks have been passed, the mixed phases A and B are compacted in the pan of the desired shapes and sizes, in the desired colours that can vary from a minimum of 2 to a maximum of 10 colours, preferably 3 colours.

The operator deposits with steel and/or aluminium tools, in the jargon called "trays", i.e. steel and/or aluminium boxes, closed at the sides like a lid of a box. On the bottom of these "trays" there are cuts shaped according to the design to be made, which allow the operator to make the colour fall directly in the pan, in turn positioned in the mould.

The operation is repeated "n" times based on the number of colours required.

Once the deposition of the colours is complete, the operator compacts the product, pressing on the start button of the machine, which compresses the powder according to the set parameters described above.

Once compacted, the product is ready for the addition of the solvent.

Determining the Amount of Solvent to be Added to the Compacted Powder

In order to establish the exact amount of solvent a compacted piece is placed on a scale, taking care to remove the tare weight of the pan. The weight is noted, which by convention is indicated as "WEIGHT 1", then, with a drop counter the suitable solvent begins to be added, which in the present example is water.

The addition of the solvent (water) continues dropwise until the product is saturated, i.e. until the surface of the product becomes glossy and begins to bleed liquid. At this point the product is weighed once again and the weight is noted, which by convention is indicated as "WEIGHT 2". The difference between "WEIGHT 2" and "WEIGHT 1" indicates the amount of solvent necessary to obtain the effect object of this invention, i.e. to obtain solid creamy powders that can be mixed to obtain new colours not initially present. For example, if WEIGHT 1 were equal to 5 g and WEIGHT 2 were 7.5 g, by subtracting one gets 2.5 g of added solvent, i.e. 33.3% with respect to WEIGHT 2.

The repetition of this operation on many samples of compacted powder makes it possible to obtain an average value of solvent to be added.

Having thus established the amount of solvent to use, it is possible to proceed with this operation on a large scale.

The pieces (compacted powders) are then transferred on an automatic dosing machine, which will add to the products the amounts of solvent determined as indicated above, depositing it through an automatic "drop counter".

Drying

At this point it passes to the last phase of the processing that consists of drying the wafer in an oven.

Formulation Example No 2—Compact Complexion Enhancer

| DESCRIPTION OF RAW MATERIALS | QUANTITY (%) |
|---|---|
| PHASE A | |
| Talc (filler) | q.s. 100 |
| Mica (CI77019) (texturiser) | 10 |
| Silica (texturiser) | 10 |
| D&C RED 7 CA lake (CI15850:1) (insoluble dye) | 10 |
| RED 33 hydro (CI17200) (soluble dye) | 0.5 |
| Red iron oxide (CI77491) (insoluble dye) | 0.5 |
| Brown iron oxide (CI77491-77492-77499) (insoluble dye) | 10 |
| Black iron oxide (CI77499) (insoluble dye) | 0.25 |
| Sorbic acid (preservative) | 0.3 |
| PHASE B | |
| Octyldodecanol (ligand) | 5 |
| Capric/caprilic triglyceride (ligand) | 12.5 |
| Polysorbate 20 (receiving liquid) | 2.5 |
| Phenoxyethanol (preservative) | 0.85 |
| PHASE C | |
| Pearlescent pigment - mica (CI77019) + titanium dioxide (CI77891) (insoluble pearlate pigment) | 20 |

Production of the Product of Example 2

After mixing phases A and B as described in example 1 and having carried out the checks after said mixing, PHASE C is added to phases A and B previously mixed.

Phase C is mixed at lower speed and in shorter times with respect to those used to mix phases A and B, to keep the pearlescent pigment integral. The speed ranges for the dispersion of PHASE C vary between 500 and 1500 revs/minute; whereas the mixing time ranges from 30 to 60 seconds.

The checks are once again repeated on the mixture obtained (necessary routine checks after mixing) as already described for example 1.

Then it proceeds as shown in example 1 to compact the mixed powder (phases A, B and C) and to determine the amount of solvent to be added to the compacted powder. Finally, there is then drying as indicated above.

The invention claimed is:

1. A method for the production of coloured cosmetic powders having a solid and creamy consistency for use on the skin of the eyes, face and body comprising the following steps:
    a) mixing a powder phase consisting of:
        from 60% to 99.5% by weight of at least one powder for cosmetic, alimentary and/or pharmaceutical use, and one or more dyes, said one or more dyes comprising at least one hydrosoluble dye or alcohol-soluble dye;
        from 0.5% to 40% by weight of ligand or mixture of ligands, said ligand or mixture of ligands containing at least one receiving liquid selected from: emulsifier, surfactant with polar nature, surfactant with amphiphile nature,
    wherein said percentages refer to the total weight of the powder phase;
    b) sieving said powder phase thus obtaining a coloured powder;
    c) assembly of the coloured powder thus obtained inside a container;
    d) compacting of the coloured powder inside the container with a pressure varying within the range of 50 kPa to 20,000 kPa;
    e) addition of one or more solvents to the compacted coloured powder obtained under item d), in a percentage quantity within the range of 10% to 50% by weight with respect to the total weight of the initial powder phase, wherein:
    said solvent is a polar solvent when said receiving liquid is an emulsifier or surfactant with a polar nature; said solvent is a mixture of water and glycols or a mixture of hydrodispersible esters when said receiving liquid is a surfactant with amphiphile nature;
    f) drying the product, with a drying temperature ranging from 25° to 100° C. so as to obtain a percentage of residual solvent ranging from 0.1% to 10% by weight with respect to the initial weight of the solvent added in phase "e".

2. The method according to claim 1, wherein the percentage of receiving liquid present in the ligand ranges from 5% to 30% with respect to the total weight of the ligand.

3. The method according to claim 1, comprising a further mixing phase c') of the coloured powder assembled inside the container.

4. The method according to claim 1, comprising a further removal phase f') of a surface layer of the compacted and dried powders in the container.

5. The method according to claim 1, wherein powders for cosmetic, alimentary and/or pharmaceutical use are raw materials in powder form that are selected from talcs, micas, acrylic polymers, corn starch, sericite, silica, zinc stearate, preservatives, cosmetic active principles having an action selected from a bleaching action, a detoxifying action, an antioxidant action, a hydrating action, a soothing action, a rubefacient action, and/or substances having an antimicrobial and antifungal functionality.

6. The method according to claim 1, wherein said dyes which are selected from non-pearlescent opaque coloured pigments, natural dyes, pearlescent colouring pigments.

7. The method according to claim 1, wherein the ligands are selected from esters of fatty acids and triglycerides, natural or synthetic waxes, alcohols, oil refining derivatives, silicon derivatives and mixtures thereof.

8. The method according to claim 1, said emulsifier or surfactant with a polar nature is selected from polysorbate-20, PEG-100 stearate, sorbitan stearate, oleth-10 phosphate and/or polyglyceryl-2 isostearate, carbon-based esters or ethers.

9. The method according to claim 1, wherein the polar solvent added in phase e) is selected from water, alcohols and hydroalcohol solutions.

10. The method according to claim 1, wherein said one or more dyes are selected from: azoic derivatives (CI15985), xanthene derivatives (CI45170), triphenylmethane derivatives (CI42090), indigo derivatives (CI73015), FD&C RED 33 (CI17200), and FD&C BLUE No.1 (CI42090).

11. The method according to claim 1, wherein said ligand or mixture of ligands is selected from: phenyl dimethicone, dimethicone, carnauba wax, octyldodecanol, vaseline oil, isononyl isonanoate, isopropyl stearate, capric/caprilic triglyceride, phenoxyethanol and/or caprilyl dimethicone and mixtures thereof.

12. The method according to claim 1, wherein said surfactant with amphiphilic nature is selected from poly-crosslinked polymer acrylates/C10-30 alkyl acrylates, poly-crosslinked polymer acrylates/vinyl isodecanoate or inulin lauryl carbamate.

13. The method according to claim 1, wherein said polar solvent is selected from isopropyl, ethyl, methyl alcohols and mixtures thereof.

14. The method according to claim 1, wherein said glycols are selected from hexylene glycol, butylene glycol, propylene glycol or pentylene glycol.

15. The method according to claim 1, wherein said hydrodispersible ester is bis-ethoxyglycol succinate.

* * * * *